United States Patent
Ii et al.

(10) Patent No.: US 10,351,507 B2
(45) Date of Patent: Jul. 16, 2019

(54) CARBONATE ESTER PURIFICATION METHOD, CARBONATE ESTER SOLUTION PRODUCTION METHOD, AND CARBONATE ESTER PURIFICATION APPARATUS

(71) Applicant: UBE INDUSTRIES, LTD., Ube-shi, Yamaguchi (JP)

(72) Inventors: Hirofumi Ii, Ube (JP); Yuya Fukui, Ube (JP); Yohei Shimasaki, Ube (JP); Koji Okano, Ube (JP); Koji Takebayashi, Ube (JP); Naoto Nakao, Ube (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 3 days.

(21) Appl. No.: 15/538,621

(22) PCT Filed: Dec. 25, 2015

(86) PCT No.: PCT/JP2015/086357
§ 371 (c)(1),
(2) Date: Jun. 21, 2017

(87) PCT Pub. No.: WO2016/104758
PCT Pub. Date: Jun. 30, 2016

(65) Prior Publication Data
US 2017/0342017 A1    Nov. 30, 2017

Related U.S. Application Data

(63) Continuation of application No. PCT/JP2015/086357, filed on Dec. 25, 2015.

(30) Foreign Application Priority Data

Dec. 26, 2014    (JP) .................................. 2014-265484

(51) Int. Cl.
*C07C 68/08*    (2006.01)
*B01D 3/16*    (2006.01)
(Continued)

(52) U.S. Cl.
CPC .............. *C07C 68/08* (2013.01); *B01D 3/009* (2013.01); *B01D 3/143* (2013.01); *B01D 3/16* (2013.01);
(Continued)

(58) Field of Classification Search
CPC ......... C07C 68/08; C07C 69/96; B01D 3/009; B01D 3/143; B01D 3/16; B01D 3/343; B01D 3/42
See application file for complete search history.

(56) References Cited

U.S. PATENT DOCUMENTS 5,380,906 A  *  1/1995  Nishihira ................ C07C 68/00
                                                    558/260
5,600,049 A  *  2/1997  Sy .............................. C07C 2/66
                                                    203/21

FOREIGN PATENT DOCUMENTS

JP    H03-027344 A    2/1991
JP    H03-120240 A    5/1991
(Continued)

OTHER PUBLICATIONS

Parkash, S, Refining Processes Handbook, 2003, Gulf Pub., 22-28 (Year: 2003).*

(Continued)

Primary Examiner — Renee Robinson
Assistant Examiner — Derek N Mueller
(74) Attorney, Agent, or Firm — Oliff PLC

(57) ABSTRACT

A carbonate ester purification apparatus including a first distillation column in which an alcohol and a first solution containing a carbonate ester and formaldehyde, or a first (Continued)

solution containing a carbonate ester, formaldehyde and an alcohol is supplied to obtain a distillate containing the formaldehyde and the alcohol from a column top part while obtaining a carbonate ester solution with a lower content of formaldehyde than in the first solution from a column bottom part, a reactor having a catalyst for producing an acetal and/or a hemiacetal by reacting the formaldehyde to the alcohol and a reflux part refluxing a fluid containing the acetal and/or the hemiacetal to the first distillation column.

7 Claims, 4 Drawing Sheets

(51) Int. Cl.
    *C07C 69/96*    (2006.01)
    *B01D 3/34*    (2006.01)
    *B01D 3/42*    (2006.01)
    *B01D 3/00*    (2006.01)
    *B01D 3/14*    (2006.01)

(52) U.S. Cl.
    CPC ............... *B01D 3/343* (2013.01); *B01D 3/42* (2013.01); *C07C 69/96* (2013.01); *Y02P 20/127* (2015.11)

(56) References Cited

FOREIGN PATENT DOCUMENTS

| | | |
|---|---|---|
| JP | H05-201932 A | 8/1993 |
| JP | H06-041021 A | 2/1994 |
| JP | H06-092910 A | 4/1994 |
| JP | H09-110807 A | 4/1997 |
| JP | 2004-323470 A | 11/2004 |
| JP | 2014-162746 A | 9/2014 |

OTHER PUBLICATIONS

Jun. 27, 2017 International Preliminary Report on Patentability issued in International Patent Application No. PCT/JP2015/086357.
Mar. 22, 2016 International Search Report issued in International Patent Application No. PCT/JP2015/086357.

* cited by examiner

CARBONATE ESTER PURIFICATION METHOD, CARBONATE ESTER SOLUTION PRODUCTION METHOD, AND CARBONATE ESTER PURIFICATION APPARATUS

TECHNICAL FIELD

The present disclosure relates to a carbonate ester purification method, a carbonate ester solution production method and a carbonate ester purification apparatus.

BACKGROUND ART

A carbonate ester is a compound useful as a synthetic raw material for aromatic polycarbonates and pharmaceuticals and agricultural chemicals. A known process for producing a carbonate ester is one that carries out a synthesis by a gas phase reaction using carbon monoxide and nitrite ester in the presence of a platinum group metal solid catalyst (see, for example, Patent Literatures 1 and 2). In such a process, a carbonate ester can be obtained by the following reaction formula (i).

$$CO + 2RONO \rightarrow ROC(=O)OR + 2NO \qquad (i)$$

In the production methods of Patent Literatures 1 and 2, an intended compound is produced by a catalytic reaction while recycling alkyl nitrite as a raw material. In such a production method, a target compound can be produced in large amounts by scaling up but there is a demand for establishment of a technical procedure for the stable continuous production. This is because once the continuous production is interrupted, cumbersome operations such as starting up and shutting down the apparatus are needed and additionally the opportunity loss caused by the operation shutdown increases.

Thus, Patent Literature 2 proposes a technical procedure for preventing the catalytic activity reduction by detecting a concentration of nitrogen monoxide in a supplied gas and adjusting an amount of the molecular oxygen to be supplied based on the obtained concentration. Patent Literature 3 proposes a technical procedure for maintaining the catalytic activity by supplying hydrogen chloride to compensate the chlorine content released from the chloride of the platinum group metal (see, e.g., Patent Literature 3).

CITATION LIST

Patent Literature

Patent Literature 1: Japanese Unexamined Patent Publication No. 2004-323470
Patent Literature 2: Japanese Unexamined Patent Publication No. 2014-162746
Patent Literature 3: Japanese Unexamined Patent Publication No. H9-110807

SUMMARY OF INVENTION

Technical Problem

In the conventional processes as in Patent Literatures 1 to 3, in order to remove water and alcohol accompanying a carbonate ester, the water and alcohol are distilled out in a distillation column to reduce impurities contained in the carbonate ester solution. However, the carbonate ester solution obtained by such a process contains a small amount of impurities such as the foilnaldehyde derived from a side reaction.

Carbonate esters, however, have been studied to be used in various fields such as the electrolyte of a lithium ion battery in addition to the synthetic raw material such as pharmaceuticals and agricultural chemicals. Accordingly, there is a demand for establishment of a technical procedure for producing a carbonate ester solution with sufficiently reduced impurities.

The technical procedure for reducing impurities from a carbonate ester includes, for example, a distillation process. However, when the distillation of a carbonate ester-containing solution obtained by the conventional production method is carried out continuously for an extended period of time, a phenomenon arises wherein inside a heat exchanger (condenser) for cooling a distillate of a distillation column and the upper part of the distillation column are blocked by scales. The scales need to be removed periodically, thus there is a situation that it is difficult to continue the carbonate ester purification for an extended period of time. For this reason, there is a demand for establishment of a technical procedure for purifying a carbonate ester stably by sufficiently preventing the scale formation.

The present invention was accomplished in light of the above situation and has an object to provide, in an aspect, a carbonate ester purification method capable of continuously carrying out the carbonate ester purification for an extended period of time and a carbonate ester purification apparatus. The present invention, in another aspect, has an object to provide a carbonate ester solution production method capable of continuously producing a carbonate ester solution with reduced impurities for an extended period of time.

Solution to Problem

The present inventors studied various causes of the scales that block a heat exchanger, the upper part of a distillation column, and the like when distilling a carbonate ester solution. As a result, it was revealed that the polymers such as paraformaldehyde produced from formaldehyde in the impurities contained in a carbonate ester are the major cause.

Under the circumstances, the present invention provides, in an aspect, a carbonate ester purification method comprising a first distillation step of supplying an alcohol and a first solution containing a carbonate ester and formaldehyde, or supplying a first solution containing a carbonate ester, formaldehyde and an alcohol to a distillation column to obtain a distillate containing the formaldehyde and the alcohol from a column top part while obtaining a carbonate ester solution with a lower content of formaldehyde than in the first solution from a column bottom part; and a reaction step of refluxing a part of a reaction product containing an acetal and/or a hemiacetal obtained by contacting the distillate with a catalyst to the distillation column while discharging a remaining part of the reaction product from the distillation column.

In the above purification method, the formaldehyde and the alcohol are reacted by contacting the distillate containing the formaldehyde and the alcohol with a catalyst, to obtain an acetal and/or a hemiacetal. Thus, the formaldehyde contained in the first solution is prevented from being concentrated in the column top part of the distillation column, the reflux part and the like. Accordingly, the formaldehyde polymer production is prevented and consequently the scale formation is reduced in the column top part of the distillation column, the reflux part and the like. In this way, the carbonate ester purification method for enhancing the purity of a carbonate ester can be carried out continuously for an extended period of time.

Some embodiments may include an alkali treatment step of mixing the first solution and an alkali to reduce acidic substances contained in the first solution before the first distillation step. Thus, the impurities such as acidic substances are reduced sufficiently.

Some embodiments may include a second distillation step of fractionating the carbonate ester solution to remove an impurity from the carbonate ester solution, the impurity being different in boiling point from the carbonate ester. Examples of the impurity include water produced when an acetal and/or a hemiacetal are obtained from the alcohol and the formaldehyde. The inclusion of the second distillation step further enables the reduction of the impurities such as water.

The present invention provides, in another aspect, a carbonate ester solution production method comprising a first distillation step of supplying an alcohol and a first solution containing a carbonate ester and formaldehyde, or supplying a first solution containing a carbonate ester, formaldehyde and an alcohol to a distillation column to obtain a distillate containing the formaldehyde and the alcohol while obtaining a carbonate ester solution with a lower content of formaldehyde than in the first solution from a column bottom part; and a reaction step of refluxing a part of a reaction product containing an acetal and/or a hemiacetal obtained by contacting the distillate with a catalyst to the distillation column while discharging a remaining part of the reaction product from the distillation column.

In the above production method, the formaldehyde and the alcohol are reacted by contacting the distillate containing the formaldehyde and the alcohol with a catalyst, to obtain an acetal and/or a hemiacetal. Thus, the formaldehyde is prevented from being concentrated in the column top part of the distillation column, the reflux part and the like. Accordingly, the formaldehyde polymer production is prevented and consequently the scale formation is reduced in the column top part of the distillation column, the reflux part and the like. In this way, the highly purified carbonate ester solution with reduced impurities can be produced continuously for an extended period of time.

Some embodiments may include an alkali treatment step of mixing the first solution and an alkali to reduce acidic substances contained in the first solution before the first distillation step. In this way, the highly purified carbonate ester solution with further reduced impurities can be produced.

Some embodiments may include a second distillation step of fractionating the carbonate ester solution to remove an impurity from the carbonate ester solution, the impurity being different in boiling point from the carbonate ester. Examples of the impurity include water produced when an acetal is obtained from the alcohol and the formaldehyde. The inclusion of the second distillation step enables the production of the highly purified carbonate ester solution with further reduced impurities.

The present invention provides, in still another aspect, a carbonate ester purification apparatus including a first distillation column in which an alcohol and a first solution containing a carbonate ester and formaldehyde, or a first solution containing a carbonate ester, formaldehyde and an alcohol is supplied to obtain a distillate containing the formaldehyde and the alcohol from a column top part while obtaining a carbonate ester solution with a lower content of formaldehyde than in the first solution from a column bottom part; and a reflux part including a reactor having a catalyst for producing an acetal and/or a hemiacetal by reacting the formaldehyde to the alcohol, and being configured to reflux a part of a reaction product containing the acetal and/or the hemiacetal to the distillation column while discharging a remaining part of the reaction product from the distillation column.

In the above purification apparatus, in addition to the first distillation column and a second distillation column, a reactor having a catalyst for obtaining an acetal and/or a hemiacetal by reacting the formaldehyde to the alcohol contained in the first solution is provided. For this reason, the formaldehyde is prevented from being concentrated in the upper part of the first distillation column and the reflux part. Accordingly, the formaldehyde polymer production is prevented and consequently the scale formation is reduced in the upper part of the distillation column and the reflux part. In this way, the carbonate ester purification can be carried out continuously for an extended period of time.

Some embodiments may be provided with a treatment tank for alkali treating of the first solution by mixing the first solution and an alkali, and a separator for removing a solid product produced by the alkali treatment. Thus, the impurities such as acidic substances are reduced sufficiently.

Some embodiments may include a second distillation column fractionating the carbonate ester solution to remove an impurity from the carbonate ester solution, the impurity being different in boiling point from the carbonate ester. Examples of the impurity include water produced when an acetal is obtained from the alcohol and the formaldehyde. The inclusion of the second distillation column enables the further reduction of the impurities such as water.

Advantageous Effects of Invention

According to the present invention, in an aspect, a carbonate ester purification method capable of continuously carrying out the carbonate ester purification for an extended period of time and a carbonate ester purification apparatus can be provided. The present invention further provides, in another aspect, a carbonate ester solution production method capable of continuously producing a carbonate ester solution with reduced impurities for an extended period of time.

DESCRIPTION OF EMBODIMENTS

An embodiment of the present invention is described in detail in reference to drawings when needed. Note that the following embodiments are examples to illustrate the present invention and not intended to limit the present invention to the following contents. In the description, the elements having the same element and the same function are denoted by the same symbols, and the description that would be redundant is omitted in some cases.

Figure 1:
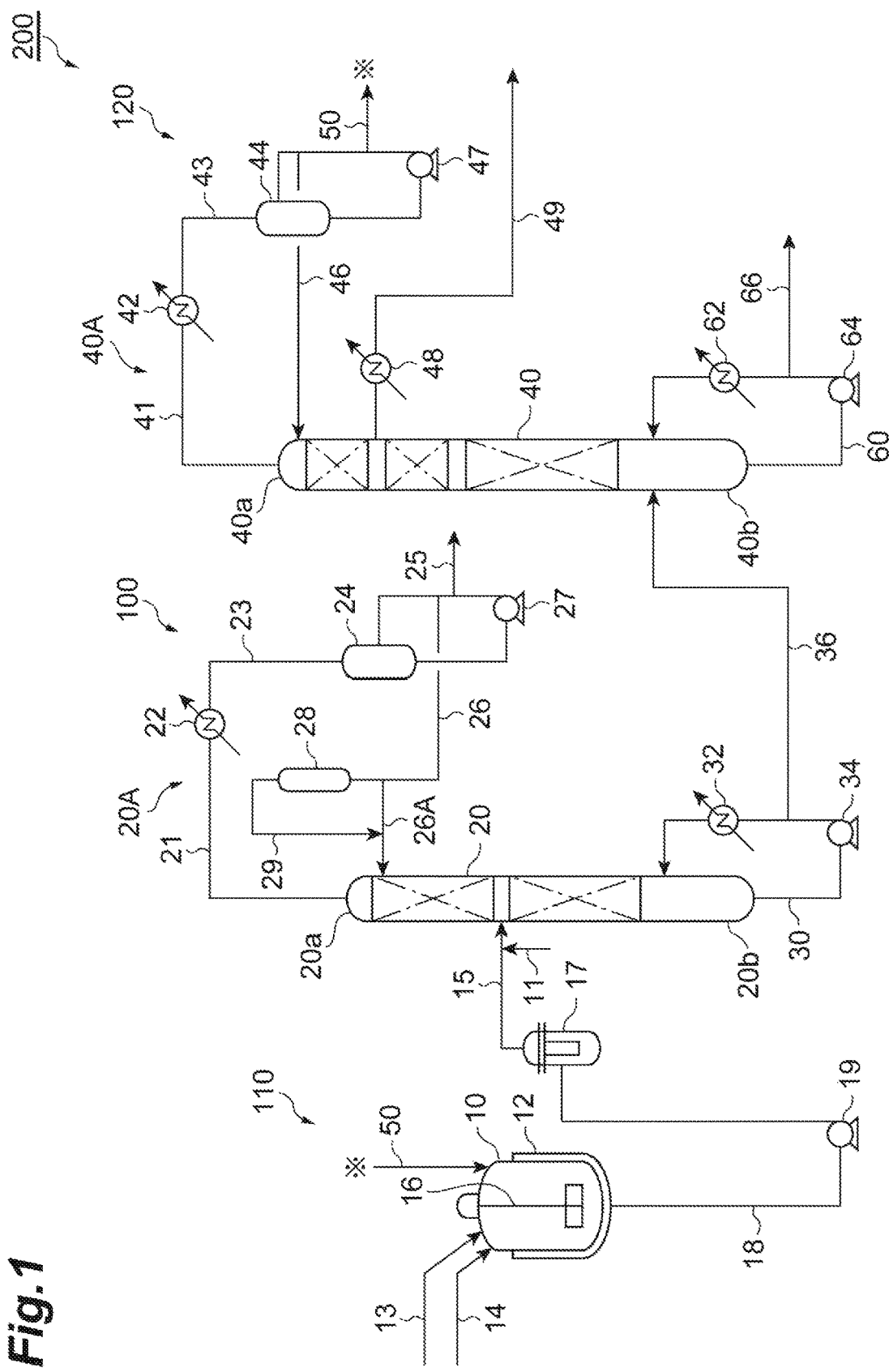
FIG. 1 is a drawing schematically illustrating an embodiment of the carbonate ester purification apparatus.

FIG. 1 is a drawing schematically illustrating an embodiment of the purification apparatus for purifying a carbonate ester. An embodiment of the carbonate ester purification method and the carbonate ester solution production method uses a carbonate ester purification apparatus 200 (carbonate ester solution production apparatus 200) illustrated in FIG. 1.

The carbonate ester purification method of the present embodiment comprises an alkali treatment step of mixing the first solution containing a carbonate ester and formaldehyde or the first solution containing a carbonate ester, formaldehyde and an alcohol with an alkali to reduce acidic substances and the like contained in the first solution, a first distillation step of supplying the first solution or the first solution and the alcohol to the first distillation column to obtain a distillate containing the formaldehyde and the alcohol from a column top part while obtaining a carbonate ester solution with a lower content of formaldehyde than in the first solution from a column bottom part, a reaction step of refluxing a part of a reaction product containing an acetal and/or a hemiacetal obtained by contacting the distillate with a catalyst to the first distillation column while discharging a remaining part of the reaction product from the first distillation column, and a second distillation step of fractionating the carbonate ester solution in the second distillation column to remove the impurities from the carbonate ester solution, the impurities being different in boiling point from the carbonate ester.

The carbonate ester purification apparatus 200 is provided with a pretreatment part 110 for carrying out the alkali treatment step, a reaction part 100 for carrying out the first distillation step and the reaction step, and a separation part 120 for carrying out the second distillation step. The first solution can be obtained by condensing the product obtained by the gas phase reaction of carbon monoxide and nitrite ester in the presence of a platinum group metal solid catalyst. The first solution contains, in addition to the carbonate ester as the main component, organic compounds such as formaldehyde, alcohols, methyl formates and methylals as sub-components, acidic substances such as chlorine compounds and nitric acid compounds and iron compounds. Of the sub-components in the first solution, the concentration of the sub-component whose boiling point is greatly different from that of the carbonate ester is adjustable using the distillation columns.

The carbonate ester is, for example, dialkyl carbonates. The two alkyl groups in a dialkyl carbonate molecule may be same or different. Examples of the dialkyl carbonate include dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonyl carbonate, ethyl methyl carbonate, and ethyl propyl carbonate.

Of the dialkyl carbonates, from the viewpoint of the reaction speed of the transesterification and easy removal of a by-produced alkyl alcohol, dialkyl carbonates having a straight chained or branch chained alkyl group having 1 to 10 carbon atoms are preferable, and dimethyl carbonate and diethyl carbonate are more preferable.

The content of the carbonate ester in the first solution is, for example, 98.0 to 99.998 mass %. The content of the formaldehyde in the first solution is, for example, 10 to 1000 mass ppm. The first solution may contain acidic substances or esters thereof in addition to the carbonate ester and the formaldehyde. Examples of the acidic substance include hydrochloric acid, nitric acid, nitrous acid, formic acid and mixtures thereof. Examples of the ester of acidic substances include nitric ester and chloroformic ester.

The total content of the chlorine compound and the nitric acid compound (including a nitrous acid compound) in the first solution is, for example, 5 to 100 mass ppm in terms of Cl and $NO_3$ or $NO_2$, respectively. The content of the iron compound in the first solution is, for example, 10 to 500 mass ppb in terms of Fe. The first solution may contain alcohols such as methanol and ethanol as the sub-component. The content of the alcohol in the first solution is, for example, 1 to 100 mass ppm.

Examples of the alkali include hydroxides of alkali metals such as sodium hydroxide (caustic soda) and potassium hydroxide (caustic potash); hydroxides of alkaline earth metals such as calcium hydroxide; alcoholates of alkali metals such as sodium methoxide and sodium ethoxide; amine compounds such as ammonia and triethylamine; and basic ion exchange resins. One of these may be used singly or two or more may be used in combination. Of the above alkalis, when an alcoholate of an alkali metal is used, the water concentration in a treatment tank 10 is sufficiently reduced.

The pretreatment part 110 is provided with the treatment tank 10 where the first solution and the alkali are mixed. Pipes 13, 14 are connected to the treatment tank 10. The treatment tank 10 is provided with a jacket 12 for allowing a heat medium to flow therethrough. The first solution is supplied to the treatment tank 10 flowing through the pipe 13. The alkali is supplied to the treatment tank 10 flowing through the pipe 14. In the treatment tank 10, the first solution and the alkali are mixed by a stirrer 16. The acidic compounds such as the chlorine compound and the nitric acid compound contained in the first solution and the alkali undergo the neutralization reaction. The acidic substances can be thus reduced in the alkali treatment step.

After the alkali treatment, the first solution is supplied to a filter 17, which is an example of the separator, flowing through a pipe 18 and a pump 19 connected to the bottom part of the treatment tank 10. The first solution is accompanied by the solid products such as inorganic chlorides and inorganic nitric acid compounds produced by the alkali treatment. For this reason, a removal step for removing at least a part of the solid products may be carried out after the alkali treatment step. More specifically, solid products such as inorganic chlorides and inorganic nitric acid compounds deposited by the alkali treatment can be removed by the filter 17. The removal of solid products as above is not indispensable but the removal of solid products can reduce the blockage frequency at the pumps and the like on the downstream side. A common metal filter may be used for the filter 17.

After the solid products are removed by the filter 17, the first solution flows through a pipe 15 and is supplied to a first distillation column 20 of the reaction part 100. At this time, an alcohol may be supplied to the first distillation column 20 separately from the first solution. As shown in FIG. 1, the alcohol may be supplied via a pipe 11 connected to the pipe 15 or may be directly supplied to the first distillation column 20 using a pipe connected to the first distillation column 20. On the other hand, when an alcohol needed to react to formaldehyde is contained in the first solution, the first solution may only be supplied to the first distillation column 20. The first distillation step can be thus carried out.

The alcohol to be supplied to the first distillation column 20 for use includes those capable of acetalizing or hemiacetalizing the formaldehyde by the catalytic reaction. Such an alcohol to be used may be, for example, aliphatic alcohols having 1 to 3 carbon atoms such as methanol or ethanol from the viewpoint of obtaining a sufficiently high reaction activity.

In the first distillation column 20, the alcohol, the formaldehyde and other trace components and the carbonate ester are fractionated based on the boiling point differences. The distillate containing the formaldehyde, the alcohol and the trace components whose boiling points are lower than the carbonate ester is introduced from a column top part 20*a* of the first distillation column 20 to the reflux part 20A provided in the first distillation column 20. The reflux part 20A is provided with a condenser 22 for cooling the distillate, a tank 24, a pump 27, a reactor 28 and a pipe that connects these mechanical pieces. The distillate discharged from the column top part 20*a* of the first distillation column 20 by a pipe 21 is cooled in the condenser 22 to be a condensate and subsequently stored in the tank 24. A part of the condensate containing the formaldehyde and the alcohol in the tank 24 is introduced from the tank 24 into the reactor 28 via the pump 27 and a pipe 26.

The reactor 28 has a catalyst for reacting the formaldehyde and the alcohol to produce at least one of an acetal and a hemiacetal. The catalyst to be used may include acid catalysts having the action that promotes the acetalization or hemiacetalization reaction. From the viewpoint of sufficiently reducing the influence to the distillation column, etc., on the downstream side, it is preferable for the catalyst, such as the solid acid catalyst, not to be dissolved in the condensate and the reaction solution containing at least one of an acetal and a hemiacetal.

The solid acid catalyst to be used is zeolites, silicas, silica-aluminas, γ-aluminas, cation exchange resins or the like. Of these, the cation exchange resin is preferable from the viewpoint of decreasing the elution of the impurities, or the like. Thus, the use of the catalyst capable of acetalizing and hemiacetalizing the formaldehyde can reduce the formaldehyde stably for an extended period of time when compared with the case where the formaldehyde is removed by adsorption.

When methanol is used as the alcohol, for example, the reaction (acetalization reaction) of the following formula (I-1) and/or the reaction (hemiacetalization reaction) of the following formula (I-2) proceeds in the reactor 28. Due to these reactions, acetals such as formaldehyde dimethyl acetal and/or hemiacetals such as formaldehyde methyl acetal are produced. Different acetals and hemiacetals may be produced depending on the type of alcohol.

$$HCHO+2CH_3OH \rightarrow CH_3OCH_2OCH_3+H_2O \quad (I-1)$$

$$HCHO+CH_3OH \rightarrow CH_3OCH_2OH \quad (I-2)$$

The reaction product containing at least one of the acetal and the hemiacetal obtained in the reactor 28 flows through a pipe 29 connected to the reactor 28 and is returned to the upper part of the first distillation column 20. The condensate from the tank 24, in addition to the above reaction product, may be returned to the upper part of the first distillation column 20 by flowing through a pipe 26A that bypasses the reactor 28. Thus, the reaction product and, in some cases, the condensate reflux to the first distillation column 20. The use of the reaction product and, in some cases, the condensate as the reflux enables an efficient fractionation in the first distillation column 20.

Thus, in the reaction step, the formaldehyde contained in the first solution is reacted to the alcohol using the catalyst to obtain an acetal and/or a hemiacetal. For this reason, the concentration of the formaldehyde in the upper part of the first distillation column 20 and the reflux part 20A can be prevented. Accordingly, the polymerization reaction of the formaldehyde is prevented thereby preventing the scales from blocking the upper part of the distillation column 20 and the reflux part 20A.

The acetalization and hemiacetalization reaction in the reactor 28 do not have to be a liquid phase reaction but may be a gas phase reaction. In such a case, the condenser 22 can be provided on the downstream side of the reactor 28 to cool the reaction product obtained in the reactor 28 in the condenser 22 and reflux to the first distillation column 20. Thus, the components whose boiling points are lower than that of the carbonate ester such as the acetal and/or the hemiacetal and the alcohol are concentrated in the upper part of the first distillation column 20 and the reflux part 20A. A part of the condensate containing these components in the tank 24 can be discharged continuously or intermittently via the pump 27 and a pipe 25 to outside of the first distillation column 20.

The discharged liquid from the pipe 25 contains, for example, the carbonate ester as the main component and may contain the formaldehyde, the acetal and/or the hemiacetal, the alcohol and water as the sub-components. The composition of the discharged liquid is identical with the composition of the reflux liquid that circulates around the reflux part 20A. The content of the formaldehyde in the discharged liquid is, for example, 20 to 100 mass ppm. The content of the carbonate ester in the discharged liquid is, for example, 90 to 99.2 mass %, and the total content of the acetal and the hemiacetal is, for example, 1000 to 5000 mass ppm. The discharged liquid from the column top part 20*a* discharged via the pipe 25 may be merged to the alcohol that flows through a pipe 316 or a pipe 319 of a production apparatus 300 of FIG. 3 to be described later.

Due to the fractionation in the first distillation column 20, the second solution containing the carbonate ester is discharged from a pipe 30 connected to a column bottom part 20*b* of the first distillation column 20. In the second solution, the components having low boiling points such as the formaldehyde and the alcohol are more reduced than in the first solution. For this reason, the purity of the carbonate ester in the second solution is higher than the first solution. Consequently, the first distillation column 20 can purify the carbonate ester and continuously produce the second solution in which the purity of the carbonate ester is higher than in the first solution. Further, the formaldehyde and the alcohol are reacted to obtain the acetal or the hemiacetal in the reactor 28 whereby the formaldehyde is sufficiently prevented from being concentrated in the upper part of the first distillation column 20 and the reflux part 20A. For this reason, the paraformaldehyde is prevented from depositing particularly in the condenser 22, enabling the carbonate ester purifying stably.

The purity of the carbonate ester in the second solution is, for example, 99.99 mass % or more. More specifically, in the second solution when compared with the first solution, the contents of the trace components such as acidic substances, alcohols, formaldehyde, iron compounds, vinyl compounds, acetals and hemiacetals are sufficiently reduced. The carbonate ester solution like this is particularly useful for the purpose where the trace components need to be sufficiently reduced (e.g., the electrolyte of a lithium ion battery).

The second solution discharged from the column bottom part 20*b* of the first distillation column 20 may contain trace components such as water produced in the above formula (I-1) with the carbonate ester as the main component. The second solution is supplied to a second distillation column 40 of the separation part 120 via the pipe 30, a pump 34 and a pipe 36. Further, a part of the second solution, after heated by the heat exchange with a heat medium at a heat exchanger 32, may be returned to the lower part of the first distillation column 20 as a heat source of the first distillation column 20.

In the second distillation column 40, the carbonate ester and the trace components contained in the second solution are fractionated based on the boiling point differences. The fluid containing the trace components having higher boiling points than the carbonate ester flows through a pipe 60 connected to a column bottom part 40b of the second distillation column 40 and are discharged via a pump 64 and a pipe 66. A part of the fluid, after heated by the heat exchange with a heat medium at a heat exchanger 62, may be returned to the lower part of the second distillation column 40 as a heat source of the second distillation column 40.

When the second solution contains the trace components whose boiling points are lower than the carbonate ester such as the alcohol (e.g., the alcohol), these trace components are introduced to the reflux part 40A that includes a condenser 42 connected to a column top part 40a of the second distillation column 40 via a pipe 41 and a tank 44 connected to the condenser 42 via a pipe 43. Specifically, the fluid from the column top part 40a of the second distillation column 40 is cooled in the condenser 42 to be a condensate and subsequently stored in the tank 44. A part of the condensate containing the trace components such as the alcohol in the tank 44 is refluxed from the tank 44 to the second distillation column 40 via a pump 47 and a pipe 46. A part of the condensate in the tank 44 may be allowed to flow through a pipe 50 and be returned to the treatment tank 10 or used for other purposes.

The carbonate ester contained in the second solution is extracted by a side cut from a pipe 49 connected to between the center section and the column top part of the second distillation column 40. The carbonate ester in the form of a gas extracted by the side cut is cooled in a heat exchanger 48 connected to the pipe 49 to be a carbonate ester solution. Thus, the content of the impurities different from the carbonate ester can be reduced sufficiently. The purity of the carbonate ester in the carbonate ester solution obtained in the second distillation column 40 is, for example, 99.995 mass % or more.

Thus, the second distillation step for obtaining the carbonate ester solution with a lower content of the impurities than in the second solution by fractionating the second solution can be carried out. The carbonate ester purification apparatus 200 is provided with the treatment tank 10, the first distillation column 20 and the second distillation column 40 separately, thereby efficiently producing the high purity carbonate ester solution continuously. In the carbonate ester solution obtained by such a purification method, trace components such as acidic substances, alcohols, formaldehyde, iron compounds, vinyl compounds, acetals and hemiacetals are sufficiently reduced. The carbonate ester solution like this is particularly useful for the purpose where the trace components need to be sufficiently reduced (e.g., the electrolyte of a lithium ion battery).

Figure 2:
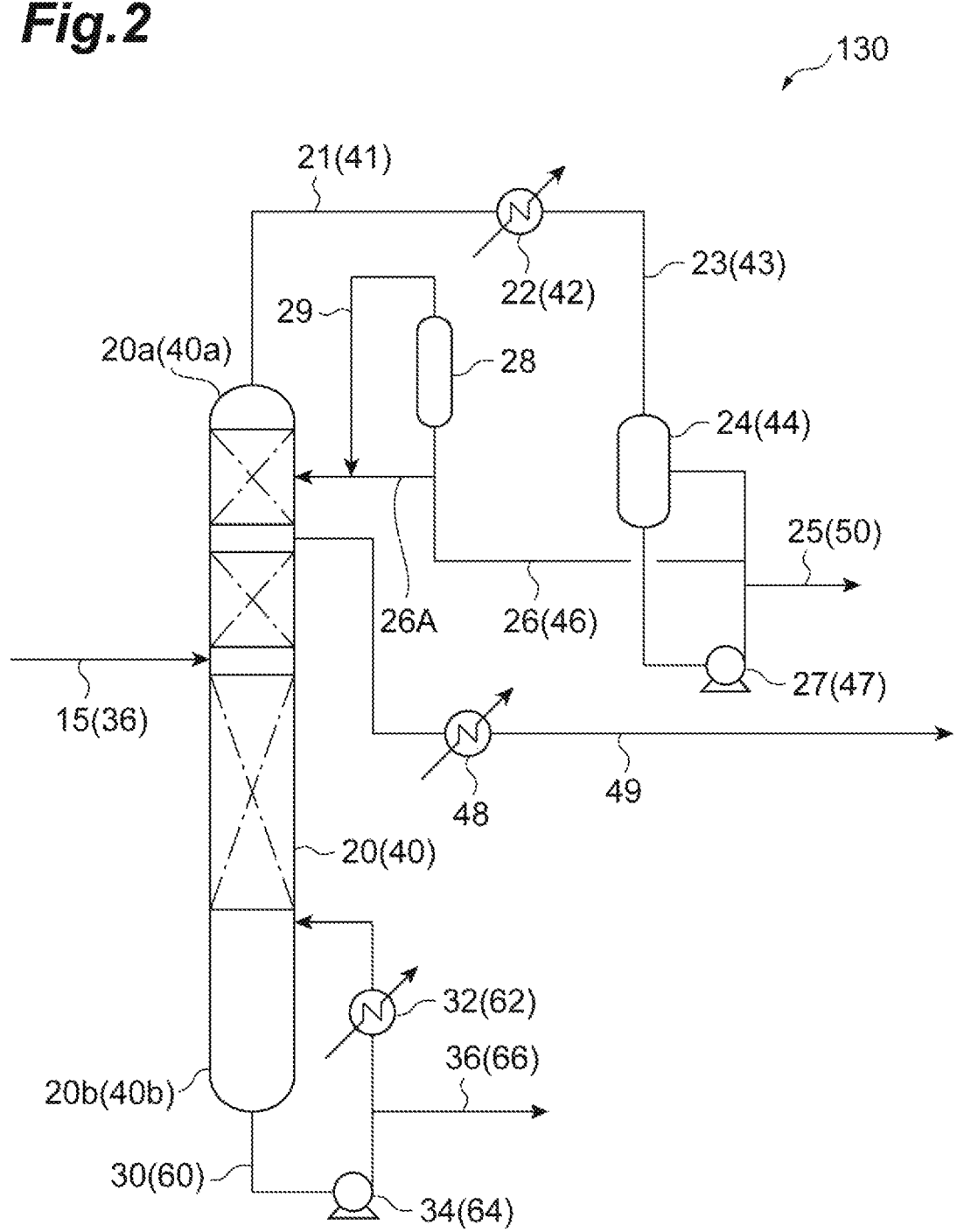
FIG. 2 is a drawing schematically illustrating another embodiment of the carbonate ester purification apparatus.

FIG. 2 is a drawing schematically illustrating another embodiment of the purification apparatus for purifying a carbonate ester. Another embodiment of the carbonate ester purification method and another embodiment of the carbonate ester solution production method can be carried out using a carbonate ester purification apparatus 130 illustrated in FIG. 2.

The carbonate ester purification apparatus 130 has the combined function of the reaction part 100 and the separation part 120 of the carbonate ester solution production apparatus 200 illustrated in FIG. 1. More specifically, the carbonate ester purification apparatus 130, where steps of the following (1) and (2) are carried out separately from a step of (3), can combine the distillation columns to one. Each step can be carried out in the same manner as in the above embodiments.

(1) A first distillation step of supplying an alcohol and a first solution containing a carbonate ester and formaldehyde, or supplying a first solution containing a carbonate ester, formaldehyde and an alcohol to a distillation column 20 to obtain a distillate containing the formaldehyde and the alcohol from a column top part 20a while obtaining a second solution with a lower content of formaldehyde than in the first solution from a column bottom part 20b (2) A reaction step of refluxing a part of a reaction product containing an acetal and/or a hemiacetal obtained by contacting the distillate with a catalyst to the distillation column while discharging a remaining part of the reaction product from the first distillation column 20

(3) A second distillation step of supplying the second solution to a distillation column 40 and removing the impurities different in boiling point from the carbonate ester from the second solution to obtain a carbonate ester solution in which the purity of the carbonate ester is higher than in the second solution When carrying out the first distillation step and the reaction step, for example, a valve provided on the pipe 49 is closed so that the heat exchanger 48 and the pipe 49 do not need to be used. Further, when carrying out the second distillation step, the condensate from the tank 44 may be refluxed in its full volume to the second distillation column 40 via the pump 47, the pipe 46 and the pipe 26A without flowing through the reactor 28. Furthermore, a part of the condensate containing the impurities such as the alcohol in the tank 44 may be allowed to flow through the pipe 50 and returned to the treatment tank 10 or used for other purposes. The impurities such as water can be discharged using pipes 60, 66 from the column bottom part 40b. Accordingly, the carbonate ester solution with sufficiently reduced impurities can be obtained as a side cut.

The configuration of the distillation column 20 (40) can be the same as that of the first distillation column 20 and the second distillation column 40 in FIG. 1. Thus, when the batch process is adopted, the distillation columns can be combined to one, hence economically advantageous.

Figure 3:
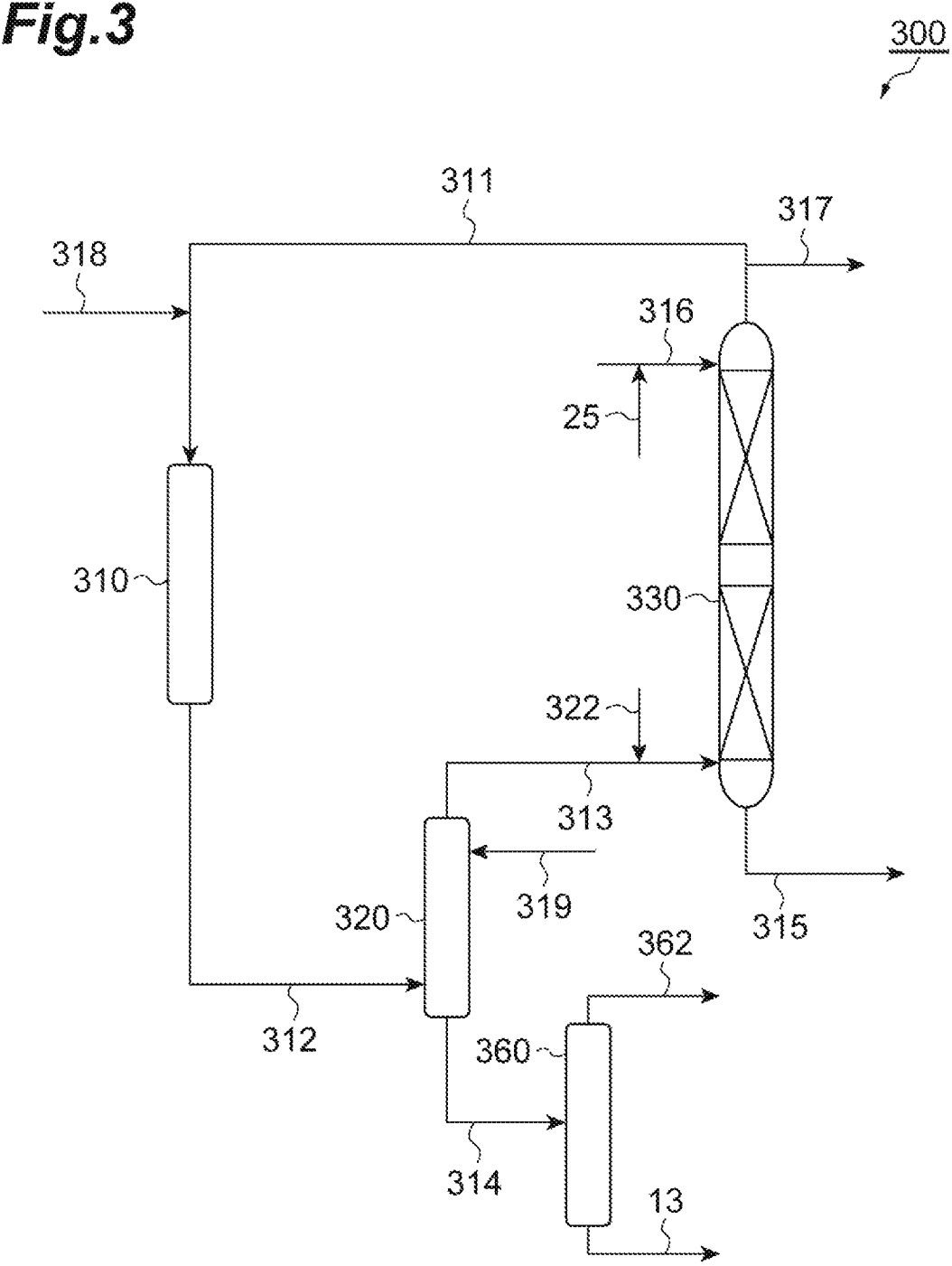
FIG. 3 is an example of an apparatus for producing the first solution containing a carbonate ester and formaldehyde.

FIG. 3 is an example of an apparatus for producing the first solution containing a carbonate ester and formaldehyde. The first solution production apparatus 300 is provided with a first reactor 310 having a catalyst for producing dialkyl carbonate and nitric monoxide by reacting carbon monoxide and alkyl nitrite and wherein a second gas containing the dialkyl carbonate and the nitric monoxide is produced from a first gas containing the carbon monoxide, the alkyl nitrite and the nitric monoxide, an absorption column 320 wherein the second gas is contacted with an absorbing liquid which absorbs the dialkyl carbonate to separate a condensate containing the dialkyl carbonate from a noncondensable gas containing the nitric monoxide and a second reactor 330 wherein a mixed gas of the noncondensable gas and a molecular oxygen and an alcohol are introduced to react to the nitric monoxide, the molecular oxygen and the alcohol thereby producing a third gas containing the alkyl nitrite and the nitric monoxide.

The first reactor 310 has a carbonate ester production catalyst for producing a carbonate ester and nitric monoxide by reacting carbon monoxide and alkyl nitrite. Examples of the carbonate ester production catalyst include solid catalysts wherein a platinum group metal and/or a compound thereof is supported on a support. The amount of the platinum group metal and/or a compound thereof to be supported in the solid catalyst relative to the support is 0.1 to 10 wt %, preferably 0.5 to 2 wt %. Examples of the support include inert supports such as activated carbons, aluminas (γ-alumina, etc.), zeolites, molecular sieves, spinels (lithium aluminate spinel, etc.). The platinum group metal and a compound thereof are supported on the support by using a known method such as an impregnation method or an evaporation to dryness method.

Examples of the platinum group metal and a compound thereof include platinum metals, palladium metals, rhodium metals and iridium metals. Examples of the platinum group metal compound include inorganic acid salts (nitrates, sulfates, phosphates, etc.), halides (chlorides, bromides, etc.), organic acid salts (acetates, oxalates, benzoates, etc.) and complexes (lithium tetrachloropalladate, sodium tetrachloropalladate) of these metals. Of these, palladium chloride or chlorine-containing complexes of palladium are preferable. It is preferable that the amount of the platinum group metal and/or a compound thereof supported on the support be 0.01 to 10 mass %, with 0.2 to 2 mass % being more preferable.

The carbonate ester production catalyst may contain, in addition to the platinum group metal and a compound thereof, copper, iron, bismuth or compounds thereof. Of these, chlorides (cuprous chlorides, cupric chlorides, ferrous chlorides, ferric chlorides, bismuth chlorides) are preferable. It is preferable that the amount of these supported on the support be "platinum group metal and a compound thereof": "copper, iron, bismuth and compounds thereof" (in terms of molar ratio of metal atoms) of 1:0.1 to 1:50, with 1:1 to 1:10 being more preferable.

The preparation method of the catalyst is not limited and, for example, the catalyst can be prepared by allowing a platinum group metal compound to be supported on the support by a known method such as an impregnation method or an evaporation to dryness method and subsequently drying the obtained support.

The first gas containing the carbon monoxide and the alkyl nitrite is introduced into the first reactor 310 provided with the catalyst described above. Accordingly, the gas phase reaction represented by the following formula (II) proceeds. In the formula (II), R represents an alkyl group. It is preferable that the number of carbon atoms of the alkyl group be 1 to 3.

$$CO + 2RONO \rightarrow ROC(=O)OR + 2NO \tag{II}$$

The content of the nitric monoxide in the first gas is, for example, 5 to 50 vol % on the basis of the total of the carbon monoxide, the alkyl nitrite and the nitric monoxide. Thus, the first gas contains the nitric monoxide in a higher concentration than the molecular oxygen. For this reason, the nitric monoxide concentration in the first gas can be easily detected with a high accuracy. The content of the carbon monoxide in the first gas is, for example, 30 to 70 vol % on the basis of the total of the carbon monoxide, the alkyl nitrite and the nitric monoxide. The content of the alkyl nitrite in the first gas is, for example, 10 to 50 vol % on the basis of the total of the carbon monoxide, the alkyl nitrite and the nitric monoxide. The first gas may contain an inert gas together with the carbon monoxide, the alkyl nitrite and the nitric monoxide. In this case, it is preferable that the concentration of the nitric monoxide in the first gas be 1 to 20 vol % on the basis of the whole first gas. Further, the concentration of the carbon monoxide in the first gas is, for example, 10 to 40 vol % on the basis of the whole first gas.

Due to the reaction represented by the above formula (II), the second gas containing the carbonate ester and the nitric monoxide is produced in the first reactor 310. The concentration of the carbon ester in the second gas is, for example, 1 to 50 vol %, and the concentration of the nitric monoxide is, for example, 1 to 20 vol %, on the basis of the whole second gas. The vol % used herein indicates the volume ratio under the standard conditions (25° C., 100 kPa).

The second gas produced in the first reactor 310 is introduced into the absorption column 320 through a pipe 312. The absorption column 320 may be any gas-liquid contactable column and examples include absorption columns of tray type such as sieve trays, bubble cap trays and valve trays, or of packed column type packed with irregular packings such as pall rings or Raschig rings, or with regular packings such as sheet-like or gauze-like plates or composite plates consisting of a combination thereof.

The second gas introduced into the lower part of the absorption column 320 via the pipe 312 from the first reactor 310 countercurrently contacts the absorbing liquid for carbonate ester absorption (hereinafter simply referred to as the "absorbing liquid") introduced from the upper part of the absorption column 320. Thus, at least a part of the carbonate ester contained in the second gas is absorbed in the absorbing liquid by allowing the second gas and the absorbing liquid to gas-liquid contact. Accordingly, a condensate that absorbed the carbonate ester and the noncondensable gas containing nitric monoxide are obtained.

Examples of the absorbing liquid used in the absorption column 320 include alcohols corresponding to the alkyl group of the carbonate ester, carbonate esters and oxalate esters.

The amount of the absorbing liquid to be supplied to the absorption column 320 is, for example, 1 to 30% on a mass basis relative to the carbonate ester in the second gas. As the alcohol, the aliphatic alcohols having 1 to 3 carbon atoms such as methanol or ethanol are preferable. From the viewpoint of easy recovery, it is preferable that an alcohol have the same alkyl group with the alkyl nitrite introduced with the carbon monoxide to the first reactor 310.

The condensate containing the absorbing liquid and the carbonate ester obtained in the absorption column 320 is extracted from a pipe 314 connected to the bottom part of the absorption column 320. The condensate is introduced into the distillation column 360 through the pipe 314. In the distillation column 360, the condensate is separated into the solution containing the absorbing liquid and the first solution containing the carbonate ester based on the boiling point differences. When a low boiling point alcohol such as methanol or ethanol is used as the absorbing liquid, the alcohol is discharged from a pipe 362 connected to the column top part of the distillation column 360 and the first solution is discharged from a pipe 13 connected to the bottom part of the distillation column 360.

The first solution may be supplied to the treatment tank 10 or may be supplied to the first distillation column 20. The content of the alcohol in the first solution can be changed by adjusting the operation conditions of the distillation column 360. The content of the carbonate ester in the first solution is, for example, 98.0 to 99.998 mass %. The content of the formaldehyde in the first solution is, for example, 10 to 1000 mass ppm.

The noncondensable gas containing the carbon monoxide obtained in the absorption column 320 flows through a pipe 313 connected to the upper part of the absorption column 320. A pipe 322 for introducing the molecular oxygen is connected to the pipe 313. The molecular oxygen supplied from the pipe 322 is mixed with the noncondensable gas to be a mixed gas. The mixed gas flows through the pipe 313 and is introduced into the second reactor 330.

The mixed gas passed through the pipe 313 is introduced to the second reactor 330 from underneath and countercurrently contacts the alcohol (ROH) introduced from the pipe 316 connected to the above of the second reactor 330, whereby the reaction represented by the following reaction formula (III) proceeds. Due to this reaction, alkyl nitrite (RONO) is produced. In the formula (III), R represents an alkyl group. R is preferably an alkyl group having 1 to 3 carbon atoms. When the production apparatus 300 seen as the whole, the second reactor 330 functions to reproduce the alkyl nitrite.

In the second reactor 330, the side reaction represented by the reaction formula (IV) may proceed. From the viewpoint of improving the efficiency of the entire facility, it is preferable to promote the reaction formula (III) than the reaction formula (IV). The mixing ratio of the nitric monoxide and the molecular oxygen in the mixed gas may be 0.08 to 0.2 mol relative to per mol of the nitric monoxide contained in the mixed gas.

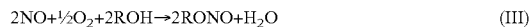
$$2NO + \tfrac{1}{2}O_2 + 2ROH \rightarrow 2RONO + H_2O \quad (III)$$

$$NO + \tfrac{3}{4}O_2 + \tfrac{1}{2}H_2O \rightarrow HNO_3 \quad (IV)$$

For the alcohol introduced from the pipe 316, an alcohol having the alkyl group of the carbonate ester produced in the production apparatus 300 is used. Examples of the alcohol include aliphatic alcohols having 1 to 3 carbon atoms such as methanol or ethanol. From the viewpoint of sufficiently proceeding the reaction of the reaction formula (III), the amount of the alcohol to be supplied to the second reactor 330 is, for example, 0.5 to 1.5 in a molar ratio relative to the supplied amount of the nitric monoxide contained in the mixed gas.

The reaction temperature at the second reactor 330 can be suitably determined in accordance with the kind of alcohol introduced from the pipe 316. When methanol is used as the alcohol, for example, the reaction temperature is, for example, 0 to 80° C. The reaction pressure is, for example, 0.1 to 1 MPa and the gas-liquid contact time is, for example, 0.5 to 30 seconds.

The third gas extracted from the upper part of the second reactor 330 contains, in addition to the alkyl nitrite produced by the reaction formula (III), nitric monoxide and trace components such as dinitrogen oxide and carbon dioxide. These trace components can be suitably discharged out of the system as an offgas from a pipe 317 branched from a pipe 311. The content of the nitric monoxide in the third gas is, for example, 5 to 50 vol % to the total of the nitric monoxide and the alkyl nitrite.

From a pipe 315 connected to the bottom part of the second reactor 330, water and the nitric acid produced by the reactions represented by the reaction formula (III) and the reaction formula (IV) and the unreacted alcohol are discharged. These components may be processed to be reused as necessary by a recovery facility provided on the downstream side. Examples of the recovery facility include those wherein water, the nitric acid and the alcohol temporarily stored in a tank are introduced to a concentration column to separate the water and the alcohol from the nitric acid whereby nitric monoxide or carbon monoxide is reacted to the nitric acid and the alcohol to produce alkyl nitrite. The thus obtained alkyl nitrite may be introduced to the second reactor 330.

The third gas flows through the pipe 311 toward the first reactor 310. The pipe 311 has a merging part with a pipe 318 which supplies the carbon monoxide, and the third gas and the carbon monoxide are mixed in the merging part. The first gas is thus obtained. The first gas is supplied to the first reactor 310.

An embodiment of the present invention is described as above but the present invention is apparently not limited to the above embodiment. In some embodiments of the carbonate ester purification apparatus, a carbonate ester with an extremely high purity can be obtained by providing the reaction part 100 and the separation part 120. However, it is not indispensable for the carbonate ester purification apparatus to be provided with the second distillation column 40. Further, it is also not indispensable for the carbonate ester purification apparatus to be provided with the pretreatment part 110. More specifically, it is not indispensable to carry out the alkali treatment step using the reaction part 100 or the second distillation step using the second distillation column 40, but the second solution obtained from the first distillation step and the reaction step can be used for various purposes as the high purity carbonate ester.

EXAMPLE

Hereinafter, the present invention is further described in detail with reference to Examples and Comparative Examples, but is not limited to these Examples.

The analysis apparatus and analysis method in each Example to be described below are as follows.

Gas chromatograph GC-2014 (trade name), manufactured by Shimadzu Corporation, was used for the content analysis of organic compounds [dimethyl carbonate, formaldehyde, methanol, dimethylene glycol dimethyl ether (DMME), methyl ethyl carbonate (MEC), methyl vinyl carbonate (MVC), formaldehyde dimethyl acetal and formaldehyde methyl acetal (hemiacetal)]. HP-INNOWAX (trade name), manufactured by Agilent Technologies, was used as the capillary column.

Moisture meter model CA-05 (trade name), manufactured by Mitsubishi Chemical Corporation, was used for the analysis of the water content. For the analysis of the chlorine compound content, a sample was first pretreated using an oxy-hydrogen combustion type apparatus for analyzing the fixed quantity of sulfur/halogen, manufactured by TOKA SEIKI CO., LTD. Subsequently, using the pretreated sample, the $Cl^-$ content was measured using ion chromatograph measurement apparatus ICS-1600 (trade name), manufactured by Nippon Dionex K.K. Ion Pac AS12A (trade name), manufactured by Thermo Fisher Scientific Inc. was used as the separation column. The $Cl^-$ measurement limit (lower limit) in this analysis was 0.01 mass ppm.

The analysis of the nitric acid compound (including the nitrous acid compound) was carried out by extracting $NO_3^-$ and $NO_2^-$ from a sample using distilled water and subsequently using the ion chromatograph measurement apparatus used for the analysis of the $Cl^-$. The nitric acid compound (including the nitrous acid compound) measurement limit (lower limit) in this analysis was 0.01 mass ppm. In the analysis of the metal (Fe), a sample was first incinerated using a quartz dish and the incinerated product was dissolved in distilled water and high purity nitric acid (content: 69 to 70 mass %) to prepare a measurement sample. The obtained measurement sample was analyzed using an ICP-MS analyzer Agilent 7700 (trade name), manufactured by Agilent Technologies.

Example 1

A formaldehyde-containing dimethyl carbonate solution (the first solution) was prepared by the process illustrated in FIG. 3. The composition of the first solution was as shown in Table 1. Methanol was added to the dimethyl carbonate solution to prepare a supply solution with a methanol content of 2 mass %. A jacketed glass tube having an inner diameter of 8 mm was packed to 10 cm with Amberlyst 15JS-HG•DRY (trade name, manufactured by ORGANO CORPORATION, styrene cation exchange resin) as the catalyst for promoting the acetalization and hemiacetalization of the formaldehyde. The supply solution was passed through the glass tube packed with the catalyst in a flow rate of 100 ml/hr while heating the catalyst by circulating warm water of 50° C. in the jacket.

At the time of having passed the solution for 1 hour, the effluent from the glass tube was analyzed. As a result, the inversion rate of the formaldehyde was 98.2 mass %, thereby revealing that the content of the formaldehyde was greatly more reduced than in the supply solution. Paraformaldehyde was not detected in the effluent. Further, the solution was continuously passed and the effluent from the glass tube was analyzed after the solution has passed for 3 hours, thereby revealing that the composition was identical with that of the effluent after the solution has passed for 1 hour.

TABLE 1

| Component | First solution |
|---|---|
| Dimethyl carbonate | 99.994% |
| Methanol | 4 ppm |
| Formaldehyde | 25 ppm |
| Water | 21 ppm |
| Chlorine compound | 1.5 ppm |
| Nitric acid compound | 0.05 ppm |
| DMME | 1 ppm |
| MEC | 3 ppm |
| MVC | 1 ppm |
| Fe | 49 ppb |
| $CH_3OCH_2OH$ | n.d. |
| $CH_3OCH_2OCH_3$ | n.d. |

Contents are mass base values.
n.d. indicates below detectable limit.

Example 2

<Alkali Treatment Step>

A stainless steel jacketed treatment tank (300 L) equipped with a thermometer and a stirrer was charged with 250 L of the dimethyl carbonate solution (the first solution) shown in Table 1. Warm water was allowed to pass through the jacket while stirring the dimethyl carbonate solution to adjust the solution temperature to be 40° C. 4.07 g of a methanol solution with a sodium methylate content of 15 mass % (equimolar to Cl of 1.5 mass ppm) was added to the dimethyl carbonate solution and continuously stirred for 1 hour. A part of the obtained treated solution was sampled and filtered, and the filtrate was analyzed. The composition of the filtrate was as shown in Table 2.

As shown in Table 2, it was verified that the addition of the alkali compound to the dimethyl carbonate solution can reduce the chlorine compound and the nitric acid compound. Additionally, it was verified that such an addition can reduce not only the chlorine compound and the nitric acid compound but also the methyl vinyl carbonate and the Fe component.

<First Distillation Step>

Figure 4:
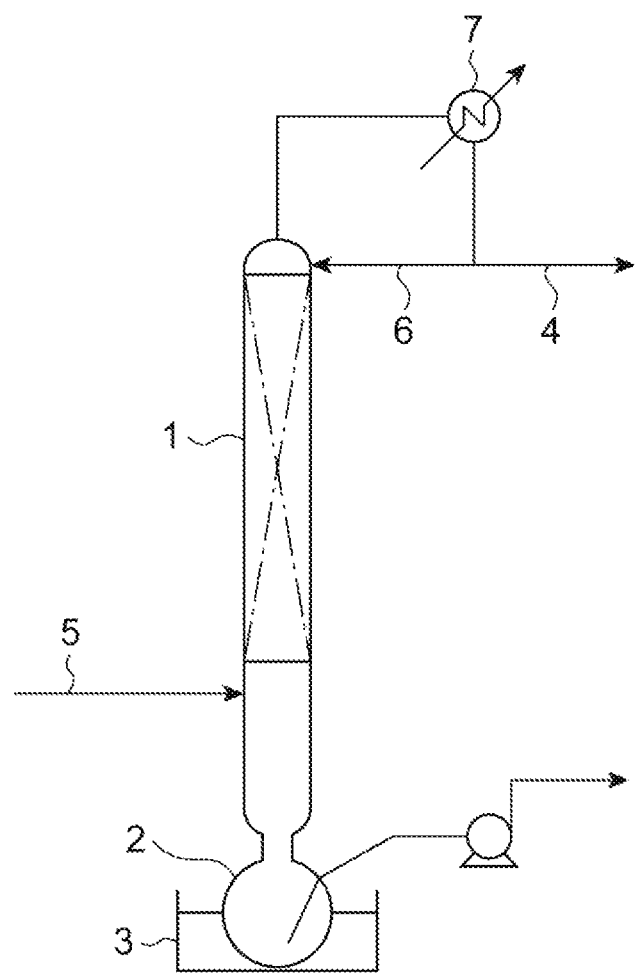
FIG. 4 is a drawing showing an experimental apparatus used in Examples.

A precisive distillation apparatus as shown in FIG. 4 was prepared. Specifically, a reflux pipe 6 of a glass distillation column 1 (inner diameter: 25 mm, packing: Sulzer EX (registered trade name, theoretical number of shelves: 16) equipped with a thermometer was packed to 10 cm³ with Amberlyst 15JS-HG•DRY (trade name, manufactured by ORGANO CORPORATION, styrene cation exchange resin) as the catalyst for promoting the acetalization and hemiacetalization of the formaldehyde. A 300 ml-round bottom flask 2 was attached to the bottom part of this distillation column 1. 200 ml of the filtrate of Table 2 was put in the round bottom flask 2.

The round bottom flask 2 was immersed in an oil bath 3, which was heated and boiled for the total reflux. The total reflux was continuously carried out until the temperature of the entire distillation column 1 reached substantially constant. When the temperature of the entire distillation column 1 reached substantially constant, the temperature of the reflux liquid was 50 to 55° C. The filtrate shown in Table 2 was continuously supplied to the middle shelf of the distillation column 1 using a pipe 5 in a flow rate of 150 ml/hour. At the same time of starting the supply, the liquid was continuously discharged from the round bottom flask 2 in such a manner that the liquid surface in the round bottom flask 2 was kept constant. A part of the reflux liquid was gradually discharged to obtain the distilled liquid while maintaining a reflux flow rate of 130 to 150 ml/hr and a column top temperature of the distillation column 1 of 89° C. or more. The discharge volume of the distilled liquid from the column top was 2 to 3 ml/hr. Table 2 shows the analysis results of the distilled liquid discharged from the column top and the liquid discharged from the bottom.

TABLE 2

| Component | Filtrate | Distilled liquid from column top | Discharged liquid from bottom |
|---|---|---|---|
| Dimethyl carbonate | 99.993% | 99.122% | 99.995% |
| Methanol | 18 ppm | 198 ppm | 2 ppm |
| Formaldehyde | 25 ppm | 48 ppm | n.d. |
| Water | 21 ppm | 17 ppm | 26 ppm |
| Chlorine compound | n.d. | n.d. | n.d. |
| Nitric acid compound | n.d. | n.d. | n.d. |
| DMME | 1 ppm | 100 ppm | n.d. |
| MEC | 3 ppm | n.d. | 3 ppm |
| MVC | n.d. | n.d. | n.d. |
| Fe | n.d. | n.d. | n.d. |
| $CH_3OCH_2OH$ | n.d. | 5 ppm | n.d. |
| $CH_3OCH_2OCH_3$ | n.d. | 6836 ppm | n.d. |

Contents are mass base value.
n.d. indicates below detectable limit.

The distilled liquid from the column top contained formaldehyde dimethyl acetal and formaldehyde methyl acetal (hemiacetal), which were the reaction products of the methanol and the formaldehyde. On the other hand, the purity of the dimethyl carbonate in the discharged liquid from the bottom was 99.995 mass %. This finding verified that the high purity dimethyl carbonate solution can be produced. Further, in the present Example, deposits were not produced on the inner wall surface of a condenser 7 during the continuous long-hour operation. This finding verified that the stable purification of the dimethyl carbonate for long hours is viable.

Comparative Example 1

Sampling was carried out by the same operation using the same apparatus as in Example 2 without packing the reflux pipe 6 with Amberlyst 15JS-HG·DRY (trade name, manufactured by ORGANO CORPORATION, styrene cation exchange resin). As shown in Table 3, the distilled liquid from the column top contained 2700 mass ppm or more of the formaldehyde. Further, when the long-hour operation was continued, a small amount of white crystal (paraformaldehyde) was deposited on the surface of the condenser 7. For this reason, the dimethyl carbonate purification could not be continued for long hours.

TABLE 3

| Component | Distilled liquid |
|---|---|
| Dimethyl carbonate | 99.120% |
| Methanol | 5840 ppm |
| Formaldehyde | 2760 ppm |
| Water | 15 ppm |
| Chlorine compound | n.d. |
| Nitric acid compound | n.d. |
| DMME | 100 ppm |
| MEC | n.d. |
| MVC | n.d. |
| Fe | n.d. |
| $CH_3OCH_2OH$ | n.d. |
| $CH_3OCH_2OCH_3$ | n.d. |

Contents are mass base values.
n.d. indicates below detectable limit.

Example 3

<Second Distillation Step>

The discharged liquid from the bottom obtained in Example 2 was supplied to a distillation column (theoretical number of shelves: 16 shelves) provided with a random packing, boiled under an ordinary pressure for the total reflux. Then, the distilled liquid was gradually discharged from the column top while maintaining a column top temperature of 90° C. or more. After discharged about 3 vol % of the supplied liquid volume from the column top, a reflux ratio was adjusted to be 1.5. Subsequently, the dimethyl carbonate solution was distilled off at a side cut arranged at a position ¼H lower from the column top (a height of ¾H from the column bottom) when the total height of the distillation column is defined as H. The composition of the dimethyl carbonate solution obtained by the side cut was as shown in Table 4.

TABLE 4

| Component | Side cut |
|---|---|
| Dimethyl carbonate | 99.998% |
| Methanol | 2 ppm |
| Formaldehyde | n.d. |
| Water | 10 ppm |
| Chlorine compound | n.d. |
| Nitric acid compound | n.d. |
| DMME | n.d. |
| MEC | 3 ppm |

TABLE 4-continued

| Component | Side cut |
|---|---|
| MVC | n.d. |
| Fe | n.d. |
| $CH_3OCH_2OH$ | n.d. |
| $CH_3OCH_2OCH_3$ | n.d. |

Contents are mass base values.
n.d. indicates below detectable limit.

As shown in Table 4, it was verified that the water content was reduced by carrying out the second distillation step. More specifically, it was verified that the second distillation step was effective in further reduction of the impurities.

Example 4

The alkali treatment step was carried out in the same manner as in Example 2. In this Example, a 500 ml-round bottom flask 2 was attached to the bottom of the distillation column 1 (theoretical number of shelves: 16 shelves) as shown in FIG. 4. Then, 300 ml of the filtrate obtained in the same manner as in Example 2 was put in the round bottom flask 2. Then, the first distillation step was carried out as described below.

The flask was immersed in an oil bath 3, which was heated and boiled for the total reflux. Subsequently, the extracting (discharging) from a pipe 4 connected to the column top was started and, at the time of discharging 10 ml, the filtrate was continuously supplied from the pipe 5 connected to the distillation column 1 in a flow rate of 150 ml/hr. The distilled liquid was extracted in a flow rate of 10 ml/hr from the pipe 4 connected to the column top while boiling so that the column top temperature reached 89° C. or more and the remaining was refluxed using the reflux pipe 6. The liquid was discharged in a flow rate of about 140 ml/hr using a pump from the column bottom part of the distillation column. After the elapse of 8 hours, the discharged liquid from the column bottom part was sampled and analyzed. As a result, the composition of the discharged liquid from the column bottom part was identical with the "discharged liquid from bottom" of Table 2.

Example 5

A precisive distillation apparatus as shown in FIG. 4 was prepared. The configuration of the precisive distillation apparatus and the catalyst were the same as in Example 2. The first distillation step was carried out in the same manner as in Example 2 without carrying out the alkali treatment step. In the present Example, the mixed solution of ethanol and the first solution used in Example 1 was used in place of the filtrate shown in Table 2. The composition of the mixed solution was as shown in Table 5. Table 5 shows the analysis results of the distilled liquid discharged from the column top and the discharged liquid discharged from the bottom of the distillation column 1.

TABLE 5

| Component | Mixed solution | Distilled liquid from column top | Discharged liquid from bottom |
|---|---|---|---|
| Dimethyl carbonate | 99.988% | 99.125% | 99.996% |
| Methanol | 56 ppm | 198 ppm | 2 ppm |
| Formaldehyde | 25 ppm | 48 ppm | n.d. |
| Water | 21 ppm | 17 ppm | 26 ppm |

TABLE 5-continued

| Component | Mixed solution | Distilled liquid from column top | Discharged liquid from bottom |
|---|---|---|---|
| Chlorine compound | 1.5 ppm | 1.2 ppm | 1.5 ppm |
| Nitric acid compound | 0.05 ppm | n.d. | 0.05 ppm |
| DMME | 1 ppm | 100 ppm | n.d. |
| MEC | 3 ppm | n.d. | 3 ppm |
| MVC | 1 ppm | n.d. | 1 ppm |
| Fe | 49 ppb | n.d. | 45 ppb |
| $CH_3OCH_2OH$ | n.d. | 5 ppm | n.d. |
| $CH_3OCH_2OCH_3$ | n.d. | 6836 ppm | n.d. |

Contents are mass base values.
n.d. indicates below detectable limit.

The distilled liquid from the column top contained formaldehyde dimethyl acetal and formaldehyde methyl acetal (hemiacetal), which were the reaction products of the methanol and the formaldehyde. On the other hand, the purity of the dimethyl carbonate in the discharged liquid from the bottom was 99.996 mass %. This finding verified that the high purity dimethyl carbonate solution can be produced. Further, in the present Example, deposits were not produced on the inner wall surface of the condenser 7 during the continuous long hour operation. This finding verified that the stable purification of the dimethyl carbonate for long hours is viable. Note that, in the present Example, the chlorine compound, the nitric acid compound and the Fe component remained in the discharged liquid from the bottom as the alkali treatment step was not carried out. However, as the concentrations thereof were considerably low, the discharged liquid can be used with no problem at all for the common purposes.

Example 6

The second distillation step was carried out in the same manner as in Example 3 except that the discharged liquid from the bottom obtained in Example 5 was used in place of the discharged liquid from the bottom obtained in Example 2. The composition of the dimethyl carbonate solution was as shown in Table 6.

TABLE 6

| Component | Side cut |
|---|---|
| Dimethyl carbonate | 99.998% |
| Methanol | 2 ppm |
| Formaldehyde | n.d. |
| Water | 10 ppm |
| Chlorine compound | 1.0 ppm |
| Nitric acid compound | 0.05 ppm |
| DMME | n.d. |
| MEC | 3 ppm |
| MVC | 1 ppm |
| Fe | 30 ppb |
| $CH_3OCH_2OH$ | n.d. |
| $CH_3OCH_2OCH_3$ | n.d. |

Contents are mass base values.
n.d. indicates below detectable limit.

As shown in Table 6, it was verified that the water content was reduced by carrying out the second distillation step. More specifically, it was verified that the second distillation step was effective in further reduction of the impurities. Note that a small amount of the chlorine compound, the nitric acid compound and the Fe was contained, as the discharged liquid, obtained in Example 5 in which the alkali treatment step was not carried out, was used in the side cut of Example 6. However, as the concentrations thereof were considerably low, the discharged liquid can be used with no problem at all for the common purposes.

Comparative Example 2

Sampling was carried out by the same operation using the same apparatus as in Example 5 without packing the reflux pipe 6 with Amberlyst 15JS-HG•DRY (trade name, manufactured by ORGANO CORPORATION, styrene cation exchange resin). As shown in Table 7, the distilled liquid from the column top contained 2700 mass ppm or more of the formaldehyde. Further, when the long-hour operation was continued, a small amount of white crystal (paraformaldehyde) was deposited on the inner wall surface of the condenser 7. For this reason, the dimethyl carbonate purification could not be continued for long hours.

TABLE 7

| Component | Distilled liquid |
|---|---|
| Dimethyl carbonate | 99.120% |
| Methanol | 5840 ppm |
| Formaldehyde | 2760 ppm |
| Water | 15 ppm |
| Chlorine compound | 1.2 ppm |
| Nitric acid compound | n.d. |
| DMME | 100 ppm |
| MEC | n.d. |
| MVC | n.d. |
| Fe | n.d. |
| $CH_3OCH_2OH$ | n.d. |
| $CH_3OCH_2OCH_3$ | n.d. |

Contents are mass base values.
n.d. indicates below detectable limit.

INDUSTRIAL APPLICABILITY

According to the present disclosure, a carbonate ester purification method capable of continuously carrying out the carbonate ester purification for an extended period of time and a carbonate ester purification apparatus can be provided. Further, a carbonate ester solution production method capable of stably producing a carbonate ester solution with reduced impurities for an extended period of time can be provided.

REFERENCE SIGNS LIST

1, 360 . . . Distillation column, 2 . . . Round bottom flask, 3 . . . Oil bath, 4, 5 . . . Pipe, 6 . . . Reflux pipe, 7 . . . Condenser, 10 . . . Treatment tank, 11, 13, 14, 15, 18, 21, 25, 26, 26A, 29, 30, 36, 46, 49, 50, 60, 66 . . . Pipe, 12 . . . Jacket, 16 . . . Stirrer, 17 . . . Filter, 20 . . . First distillation column (distillation column), 20A . . . Reflux part, 22, 42 . . . Condenser, 24, 44 . . . Tank, 27, 34, 47, 64 . . . Pump, 28 . . . Reactor, 32, 62 . . . Heat exchanger, 40 . . . Second distillation column (distillation column), 48 . . . Heat exchanger, 100 . . . Reaction part, 110 . . . Pretreatment part, 120 . . . Separation part, 130, 200 . . . Purification apparatus, 300 . . . Production apparatus, 310 . . . First reactor, 320 . . . Absorption column, 330 . . . Second reactor.

The invention claimed is:

1. A carbonate ester solution production method comprising:
   a first distillation step of supplying an alcohol and a first solution containing a carbonate ester and formaldehyde, or supplying a first solution containing a carbonate ester, formaldehyde and an alcohol to a distillation column to obtain a distillate containing the formaldehyde and the alcohol from a column top part and to introduce the distillate to a reflux part including a reactor having a catalyst while obtaining a carbonate ester solution with a lower content of formaldehyde than in the first solution from a column bottom part; and a reaction step of refluxing a part of a reaction product containing an acetal and/or a hemiacetal obtained by contacting the distillate with the catalyst to the distillation column while discharging a remaining part of the reaction product from the reflux part.

2. The carbonate ester solution production method according to claim 1, comprising an alkali treatment step of mixing the first solution and an alkali to reduce an acidic substance contained in the first solution before the first distillation step.

3. The carbonate ester solution production method according to claim 1, comprising a second distillation step of fractionating the carbonate ester solution to remove an impurity from the carbonate ester solution, the impurity being different in boiling point from the carbonate ester.

4. The carbonate ester solution production method according to claim 2, comprising: a second distillation step of fractionating the carbonate ester solution to remove an impurity from the carbonate ester solution, the impurity being different in boiling point from the carbonate ester.

5. A carbonate ester purification apparatus comprising:

a first distillation column in which an alcohol and a first solution containing a carbonate ester and formaldehyde, or a first solution containing a carbonate ester, formaldehyde and an alcohol is supplied to obtain a distillate containing the formaldehyde and the alcohol from a column top part of the first distillation column while obtaining a carbonate ester solution with a lower content of formaldehyde than in the first solution from a column bottom part of the first distillation column;

a first reflux part including a reactor having a catalyst for producing an acetal and/or a hemiacetal by reacting the formaldehyde to the alcohol, and being configured to reflux a part of a reaction product containing the acetal and/or the hemiacetal to the distillation column while discharging a remaining part of the reaction product from the first reflux part;

a treatment tank for alkali treating the first solution by mixing the first solution and an alkali, as a pretreatment part adapted for producing the first solution prior to supplying it to the first distillation column;

a separator for removing a solid product produced by the alkali treatment, the separator being a filter;

a second distillation column adapted for receiving a second solution discharged from the column bottom part of the first distillation column, and having a pipe connected to a column bottom part thereof and a pipe connected to the column at a location between a center part and the column top part thereof to extract the carbonate ester by a side cut; and a second reflux part connected to the column top part of the second distillation column.

6. The carbonate ester purification apparatus according to claim 5, wherein the second distillation column is configured for fractionating the carbonate ester solution to remove an impurity from the carbonate ester solution, the impurity being different in boiling point from the carbonate ester.

7. The carbonate ester purification apparatus according to claim 5, additionally comprising a pipe connecting the reflux part of the second distillation column and the treatment tank, wherein the pipe allows condensate condensed in the reflux part to flow through the pipe into the treatment tank.

* * * * *